(12) United States Patent
Ragno et al.

(10) Patent No.: US 10,943,694 B2
(45) Date of Patent: Mar. 9, 2021

(54) AUTOMATED INCIDENT RESPONSE METHOD AND SYSTEM

(75) Inventors: John Ragno, Hamilton, NJ (US); Hugh Hall, Upper Montclair, NJ (US)

(73) Assignee: VITALCLICK LLC, Upper Montclair, NJ (US)

( * ) Notice: Subject to any disclaimer, the term of this patent is extended or adjusted under 35 U.S.C. 154(b) by 1127 days.

(21) Appl. No.: 12/433,056

(22) Filed: Apr. 30, 2009

(65) Prior Publication Data

US 2009/0276489 A1 Nov. 5, 2009

Related U.S. Application Data

(60) Provisional application No. 61/049,112, filed on Apr. 30, 2008.

(51) Int. Cl.
*G16H 40/67* (2018.01)

(52) U.S. Cl.
CPC .................................. *G16H 40/67* (2018.01)

(58) Field of Classification Search
None
See application file for complete search history.

(56) References Cited

U.S. PATENT DOCUMENTS

| | | | |
|---|---|---|---|
| 7,221,928 B2 * | 5/2007 | Laird et al. ................. | 455/404.1 |
| 7,379,879 B1 * | 5/2008 | Sloo ............................. | 705/325 |
| 7,596,608 B2 * | 9/2009 | Alexander et al. .......... | 709/217 |
| 2002/0065855 A1 * | 5/2002 | Meyers et al. ............... | 707/530 |
| 2002/0084900 A1 * | 7/2002 | Peterson ................ | G06Q 10/06 340/573.1 |
| 2003/0135324 A1 * | 7/2003 | Navab .......................... | 701/207 |
| 2006/0255927 A1 * | 11/2006 | Dilbeck et al. .............. | 340/506 |
| 2007/0016458 A1 * | 1/2007 | Angle ..................... | G06Q 10/10 705/325 |
| 2007/0072583 A1 * | 3/2007 | Barbeau ............ | H04M 3/42348 455/404.2 |
| 2007/0278044 A1 * | 12/2007 | Hikita et al. ................. | 187/247 |
| 2007/0296575 A1 * | 12/2007 | Eisold et al. ............ | 340/539.16 |
| 2007/0298758 A1 * | 12/2007 | Verma et al. ............... | 455/404.1 |

* cited by examiner

*Primary Examiner* — Andrew B Whitaker
(74) *Attorney, Agent, or Firm* — Arent Fox LLP

(57) ABSTRACT

An automated emergency response method and system to remotely and timely update emergency response protocols, such as Emergency Medical Dispatch Protocol Reference Systems (EMDPRS), is provided. A method and system to remotely and timely update the EMDPRS in a controlled, consistent and timely manner is also provided. A method that can provide accurate, up-to-date and consistent EMDPRS provides the advantage of increasing operator readiness and efficiency in responding to an emergency, and increases the chances of success in dealing with the emergency.

26 Claims, 8 Drawing Sheets

☐ Emergency Medical Dispatch — ◻ ◰ ✕

Traumatic Incident Types

| Animal Bites | Assault / Domestic / Sexual | Bleeding / Laceration |
| --- | --- | --- |
| Burns | Eye Injuries | Fall Victim |
| Heat / Cold Exposure | Industrial Accident | Stabbing / Gunshot Victim |
| Traumatic Injury | Vehicle Related Injuries | |

All Callers Interrogation

General Questions

Miscellaneous

| Aeromedical Dispatch | Aircraft / Terrorism | Hazmat |

Medical Chief Complaint Types

| Abdominal Pains | Allergies / Stings | Back Pain | Breathing Problems | Chest / Heart Problems |
| --- | --- | --- | --- | --- |
| Diabetic Problems | Headache | OD / Poisonings / Ingestion | Psychiatric / Behavioral Problems | Seizures / Convulsions |
| Sick Person | Stroke / CVA | Unknown / Man Down | | |

Time/Life Critical Events

| Cardiac Arrest | CO Poisoning / Inhalation / Hazmat | Choking | Drowning | Electrocution | Pregnancy / Childbirth | Unconscious / Fainting |

Language: [English ▾]   [Apply]   [About]

🏁 start                                                                 9:56 PM

Fig. 6A

Emergency Medical Dispatch

Tipos de Incidentes Traumatico

| Mordeduras de Animal | Agresion/ Domestica/ Sexual | Hemorragia/ Laceracion |
| --- | --- | --- |
| Quemaduras | Heridas Oculares | Victima de Caida |
| Exposicion al Calor / Frio | Accidente Industrial | Apunalamiento / Herida de Bala |
| Herida Traumatica | Heridas Vehiculares | |

Preguntas Para Todos que Llaman

Preguntas Generales

Miscelaneo

| Despacho Aeromedico | Terrorismo/ Avion | Materiales Peligrosos |
| --- | --- | --- |

Tipos Principales de Quejas Medicas

| Dolor Abdominal | Alergias/ Picaduras | Dolor de Espalda | Problemas Respiratorios | Problemas de Pecho/ Cardiovasculares |
| --- | --- | --- | --- | --- |
| Problemas Diabeticos | Dolor de Cabeza | Sobredosis / Envenenamiento / Ingestion | Problemas Psiquiatricos y de Comportamiento | Ataques Epilepticos / Convulsiones |
| Persona Enferma | Apoplejia / ACV (Accidente Cerebrovascular) | Desconocido / Hombre Herido | | |

Acontecimientos Graves que Perjudican la Vida

| Para Cardiaco | Atragantamiento | Monoxido de carbono / Inhalacion / Material peligroso | Ahogamiento | Electrocutacion | Embarazo / Parto | Inconsciente / Desmayos |
| --- | --- | --- | --- | --- | --- | --- |

Language: Spanish    Apply    About

Fig.6B http://www.vitalclick.com - EMD Web - Microsoft Internet Explorer

File  Edit  View  Favorites  Tools  Help

Stroke CVA

Back to Main Screen

KEY

- Abdominal Pain — Is patient alert?
- Back Pain — Is patient breathing normally? (Consider BREATHING CARD)
- Breathing Problems — Describe what the patient looks like.
- Chest Pain — What is the patient doing?
- Heart Problems — Can the patient respond to you and follow simple commands?
- Diabetic Problems — Can the patient answer your questions?
- Headache — How is the patient acting?
- Seizures Convulsions — If acting unusually, what is different?
  - Is the patient able to speak in full sentences?
  - Does the patients speech sound normal?

Is the patient complaining of any pain? Where is the pain located?
(Consider appropriate CARD - BACK, CHEST, ABDOMEN)
Has the patient had a headache? (Consider HEADACHE CARD)
Has the patient had any recent injury/trauma?
Does the patient have any other medical or surgical history? What?
Has the patient had a stroke before?

SIMULTANEOUS ALS/BLS

BLS DISPATCH

DISPATCH
- Unconscious/not breathing normally.
- Marked change in level of consciousness.
- New onset of one sided weakness with paralysis, facial droop, slurred speech.

Past history of stroke (CVA) with no new changes.

[Pre-Arrival Instructions]

[Back]

start

Fig. 7

AUTOMATED INCIDENT RESPONSE METHOD AND SYSTEM

This invention claims priority from provisional U.S. Patent Application No. 61/049,112 titled "Automated Incident Response Method and System," filed on Apr. 30, 2008, and which is incorporated herein by reference in its entirety.

BACKGROUND OF THE INVENTION

Field of Invention

This invention relates to an automated emergency response method and system to remotely and timely update emergency response protocols. More specifically, this invention relates to a method and system to remotely and timely update Emergency Medical Dispatch Protocol Reference Systems (EMDPRS) in a controlled, consistent and timely manner.

Background Art

The National Highway Traffic Safety Administration (NHTSA) establishes the current national standard for emergency responses and recommends the use of a set of systematized EMDPRS by emergency medical dispatchers. The use of standardized and medically approved EMDPRS guarantees the accuracy and consistency of the medical information provided by the dispatchers when answering emergency calls. These NHTSA-standard EMDPRSs include initial response configurations that are pre-determined and tested in the field for applicability to the local community. Currently, the majority of these emergency protocols is paper-based, uses "hard cards," which are fixed protocols often outdated, and are read out loud by an emergency medical dispatcher when answering an emergency medical call.

In the Emergency Medical Services profession, it is critical that dispatchers are provided with the most up-to-date medical protocols to deal with any given emergency. Up-to-date medical protocols are especially critical during life and death situations, when a dispatcher may be required to provide potentially lifesaving instructions over the telephone. The National Standards also require changes when in the best interest of the system and to improve protocol accuracy, changes should be made to the EMDPRS, thereby specifically improving on patient care issues. Changes are also required when new information becomes available that make protocols out-of-date when compared to current medical and scientific knowledge. For example, the recent changes in Cardio-Pulmonary Resuscitation (CPR) technique represent one such example of a need for EMDPRS modification and regular updating. Additionally, and with respect to, for example, a pandemic influenza, the problem is compounded by the fact that there is no know predetermined pandemic influenza symptom set in advance of an outbreak.

Accordingly, large scale changes and/or updates to current "hard card" systems are difficult to implement because each one of the hard cards must be updated. These current paper-based EMDPRS guide card systems, or hard cards, lack the flexibility and scalability to guarantee timely, consistent, and evolving updates, in accordance with both national and local standards, especially during a period of national crisis such as, for example, a pandemic flu epidemic or other catastrophic emergency.

SUMMARY OF THE INVENTION

In view of the above problems and shortcomings, a suitable method and system that can provide accurate, up-to-date and consistent EMDPRS provide the advantage of increasing operator readiness and efficiency in responding to an emergency call, and are necessary to increase the chances of success in dealing with the emergency. Such a method and system may greatly improve national and international response to a pandemic such as, for example, a pandemic influenza, and greatly increases the chance, at a national and international level, of containing and mitigating the effects of a pandemic.

The design and construct of a local community's EMDPRS may also allow for organized and uniform methods of recommending and/or making changes to the EMDPRS. The national standards specifically stress that minor changes to the content, order or presentation of the emergency instructions can change the outcome of an event. Therefore, among other things, a suitable method that provides for the organized and uniform modification and update of an agency's existing EMDPRS in a timely fashion increases operator readiness and efficiency in responding to an emergency call, and increases the chances of success in dealing with the emergency. Aspects of the present invention provide for timely, uniform and organized updates/modifications of emergency protocols according to evolving national and local standards.

For example, an influenza pandemic could adversely impact the nation, its health care delivery systems, its transportation systems, its economy and its social structure. In accordance with the National Strategy for Pandemic Influenza Implementation Plan (Plan) published on May 3, 2007, the NHTSA was delegated, among other things, the responsibility of developing model pandemic influenza protocols (for statewide adoption) within 12 months. According to the Plan, dispatchers must have accurate, up-to-date information to be effective in call taking, dispatching and relaying information to the public. The Plan also requires that a response to pandemic influenza should be flexible, scaleable, dynamic and timely, with the ability to change rapidly based upon new information about the virus. The ability to be flexible and quickly respond to an emergency requires for protocols and algorithms to be updated readily and rapidly as more up-to-date information is obtained about the virus. A method may be put in place to quickly educate emergency call takers on the updated information, so the public is provided with current and accurate information when dealing with an emergency. According to the Plan, "just-in-time" training and education refers to the timely provision of information and instructions as they become available, and when users need them. Therefore, among other things, a suitable method that provides for the organized and uniform modification of an agency's existing EMDPRS in a timely fashion increases operator readiness and efficiency in responding to an emergency, and increases the chances of success in dealing with an emergency such as, for example, a pandemic influenza. Aspects of the present invention allow for timely, consistent and evolving updates, and also provide for simultaneous real-time instructions at the time of update/modification. "Vital-Training" may be a protocol implementation component of the invention.

While a standard set of national protocols is not always feasible because of the sometimes unique local system configurations and available resources, local agencies are nevertheless currently required to use a single, uniform, consistent and up-to-date EMDPRS within their respective jurisdictions. This presents a problem for the implementation of the Plan, and for the Emergency Medical Services profession. For example, the Plan requires uniform, consistent, up-to-date protocols, but also concurrently demands local customizations. This problem is compounded by the use of hard cards, which are fixed protocols, that are not flexible and easy to update on a national scale, and by the Plan's requirement that a response to, for example, pandemic influenza, should be flexible, scalable, dynamic, and timely, with the ability to change rapidly based on new up-to-date information about the virus causing the pandemic. Given that the EMDPRS is an integral component of any EMS response, a suitable method that provides for the timely, uniform and up to date modification of an agency's existing EMDPRS, in accordance with international, national and local standards, is required. Instead of relying on hard cards or fixed protocols that cannot be easily changed or updated, a database may be used to maintain emergency protocols for one or more local agency's EMDPRS. Aspects of the present invention provide an automatic redundancy of an agency's existing EMDPRS in that the above-described aspects of the invention provide a backup system to the currently used "hard card" EMDPRSs. Aspects of the present invention also provide for the ability to use multiple languages, thereby increasing multi-lingual operator readiness and efficiency in responding to an emergency, and increasing the chances of success in dealing with an emergency such as, for example, a pandemic influenza.

Aspects of the present invention also provide for the integration of the method and system with the National Incident Management System and/or the Center for Disease Control, as well as other partners of the Plan, via a network such as the Internet, and provide the ability to update and/or modify the various emergency response protocols in a timely and consistent manner to mirror changes in the nature of the emergency. The collection of pertinent real-time virus or other emergency-related data that can be analyzed and relayed to other partner agencies for early detection and situational awareness can also be achieved. In other words, the simultaneous compliance with both current evolving national and local standards can be ensured. Timely updates can be performed consistently in accordance with changes and updates in national EMD standards, and can be applied in real time, or at least in very short amounts of time, to any existing local EMDPRS software application.

Aspects of the present invention may also include a software application, using a Graphic-User-Interface (GUI), based on a web-based system that allows for the syndication of the software application to automate a given agency's unique suite of EMDPRS via a network such as, for example, the Internet. Thus, through a single web-based user interface, aspects of the present invention provide for uniform updates of the content of an EMDPRS software application such as, for example, new or updated emergency response protocols, in a timely manner, and transmit the updated content to desktop applications, web-based users, or any mobile devices such as, for example, portable computers, cell phones, personal digital assistants, and the like, or any emergency responders that are connected via a network such as, for example, the Internet anywhere in the United States, and possibly abroad. Also, software applications that automate any EMDPRS currently utilized are within the scope of aspects of the present invention.

With respect to private users, aspects of the present invention may also provide, through a single web-based user interface, for the transmittal of a private Emergency Medical Protocol Reference application to desktop applications, web-based users, or any mobile devices such as, for example, portable computers, cell phones, personal digital assistants, and the like. The transmittal of an emergency medical protocol in the form of an animated video demonstration and/or voice instructions to desktop applications, web-based users, or any mobile devices such as, for example, portable computers, cell phones, personal digital assistants, and the like, is contemplated. Animated demonstrations may be included, with voice overlay for CPR and choking instructions, for example, and/or terrorism response and fire evacuation protocols, among other emergencies. Integration with Emergency Response Personnel on the scene for real-time protocol updates can be performed, and commercial customer access to an Emergency Medical Protocol Reference application can be provided, which renders giving emergency response instructions, such as potentially lifesaving CPR or choking instructions accessible, consistent and accurate.

A retail version of an Emergency Medical Protocol Reference application may also be provided to desktop applications, web-based users, or any mobile devices such as, for example, portable computers, cell phones, personal digital assistants, and the like. An emergency medical protocol may be transmitted in the form of an animated video demonstration and/or voice instructions to desktop applications, web-based users, or any mobile devices such as, for example, portable computers, cell phones, personal digital assistants, and the like. Animated demonstrations may be included, with voice overlay for CPR and choking as well as terrorism and fire evacuation protocols, and may provide for integration with Emergency Response Personnel on the scene for real-time protocol updates. Thus, a retail customer may be allowed access to an Emergency Medical Protocol Reference application to receive consistent and accurate lifesaving CPR or choking response instructions.

Other aspects of the present invention may provide a customized suite of customer specific instructions, procedures, manuals and the like, covering a broad spectrum of areas and disciplines based on a web-based software system that allows for the syndication of a custom instructional protocol reference application via a network, such as the Internet. Thus, through a web-based user interface, a customized suite of customer-specific interactive instructional applications can be transmitted to desktop applications, web-based users, or any mobile devices such as, for example, portable computers, cell phones, personal digital assistants, and the like. Aspects of the present invention allow for the transmittal of an interactive instructional/repair manual application, including animated video demonstration and/or voice instructions to desktop applications, web-based users, or any mobile devices such as, for example, portable computers, cell phones, mobile devices, personal digital assistants, and the like. The animated demonstrations can have voice overlay. A database may be used to maintain the protocols, instructions, and prompts for a given customer's suite of instructions or protocols. Thus, a customer can have access to a customized application which makes giving instructions, procedures and protocols accessible, consistent and accurate. Other aspects of the present invention provide an application development tool that can create customized applications for customers, which can include animated demonstrations (e.g., video) and/or audio instructions or protocols.

Examples of software used to modify or customize the EMD protocols include "Main Screen Management," "Face Card Management," "Face Card—Pre-Arrival Instructions Management," "Prompt Management" and "Language" functionality. The design of certain features, in accordance with aspects of the invention, allows the development of customized electronic EMDPRS applications specific to each locality.

BRIEF DESCRIPTION OF THE DRAWINGS

Various exemplary aspects of the systems and methods will be described in detail, with reference to the following figures, wherein:

FIGS. 6A-6B are illustrations of screen graphical interfaces in English and in Spanish, according to various aspects of the present invention; and FIG. 7 is an exemplary screen graphical user interface of emergency response instructions, according to various aspects of the present invention.

DETAILED DESCRIPTION

These and other features and advantages of this invention are described in, or are apparent from, the following detailed description of various exemplary aspects of the systems and methods according to this invention.

Figure 1:
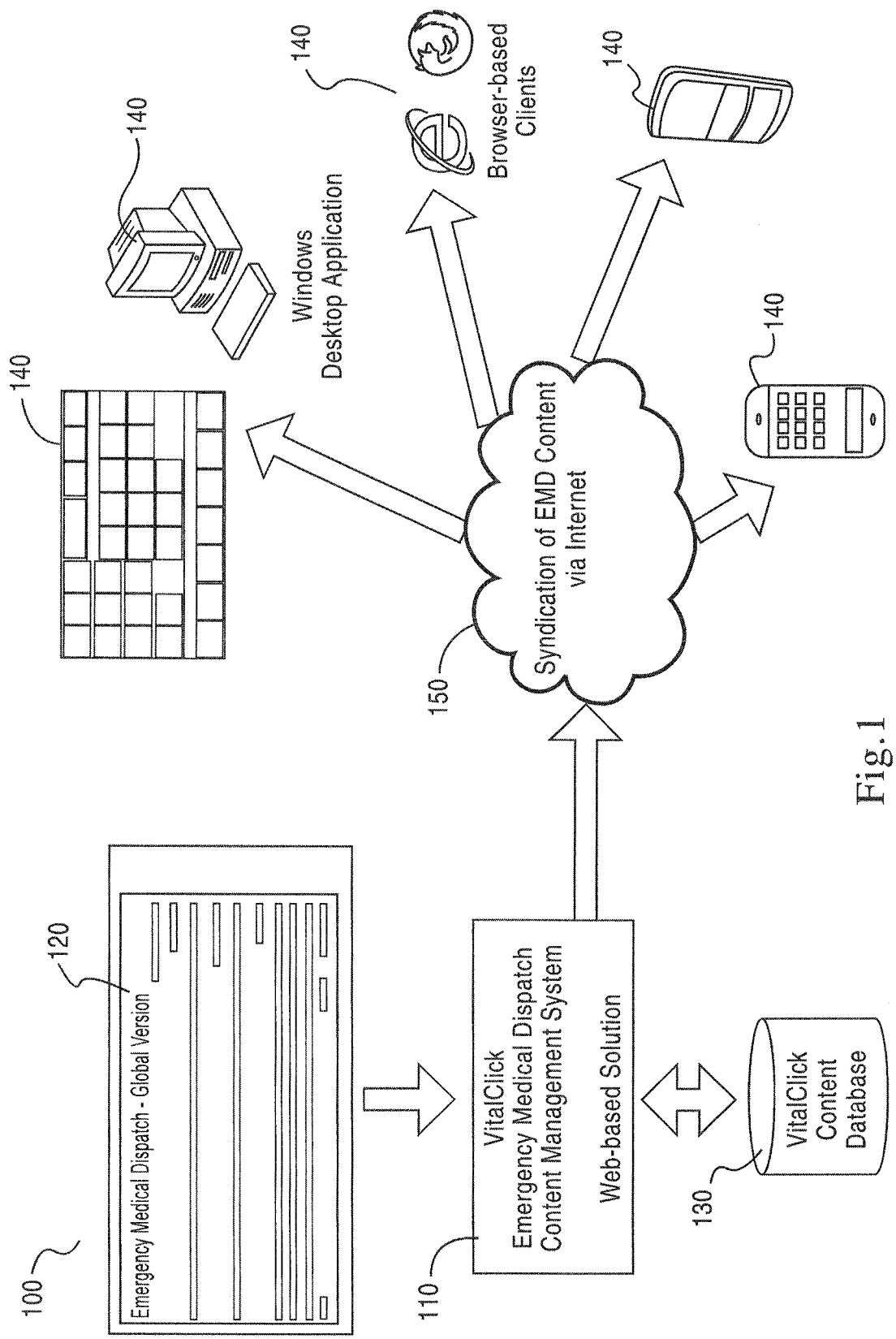
FIG. 1 is a diagram illustrating an exemplary system for providing incident response in accordance with various exemplary aspects of the present invention.

FIG. 1 is a diagram illustrating an exemplary method of providing incident response in accordance with aspects of the present invention. In FIG. 1, the system 100 comprises an Emergency Medical Dispatch Protocol Reference System (EMDPRS) content management system 110 that contains updated emergency protocols 120 for a wide variety of possible emergencies, as discussed in more detail below. The emergency protocols 120 may be stored in a database 130, and may be updated consistently with evolving national and local standards at regular intervals or whenever a new development in these standards occurs. For example, emergency protocols 120 can be updated timely and consistently with the requirements of the NHTSA. More specifically, updated and targeted protocols can be transmitted instantaneously to various responders such as, for example, emergency medical dispatchers, or users in response to a specific emergency such as, for example, pandemic influenza in the Southwest. According to various aspects of the present invention, the EMDPRS content management system 110 can transmit the content of the emergency protocols 120 to various recipients 140, such as, for example, desktop applications, cell phones, personal digital assistants, mobile devices, other web-based systems, and the like, or any other emergency responders or clients.

According to various aspects of the present invention, the emergency responders can be, for example, local 911 centers, but the responders can also be individual persons, or groups of persons, having access to a mobile device 140 that is connected to the dispatch center 110. The emergency protocols 120 may be updated, for example, in response to modifications in national standards with respect to specific emergency situations. Emergency protocols 120 may provide instructions, for example, on how to respond to pandemic influenza, but may also provide instructions on how to perform a Heimlich maneuver when someone is choking, on how to perform CPR, or other emergency response instructions.

In cases of, for example, pandemic influenza, which typically goes through several stages, the emergency protocols 120 may be updated in real time and in response to the various stages of the pandemic, according to various aspects of the present invention. For example, a protocol that is appropriate for stage 1 of the pandemic may no longer be appropriate for stage 3 of the pandemic, and aspects of the present invention allow for the update of the emergency protocols 120, so that the responders/recipients 140, such as, for example, 911 operators or responders on the field, may have an appropriate response to the changing pandemic in real time and as the pandemic is evolving. According to various aspects of the present invention, the responders/recipients 140 may thus be provided with the proper protocols to deal with the current stage of the pandemic in real time. Such real time response is possible because the emergency protocols 120 provided via the dispatch center 110 can be updated almost instantaneously to correspond to the current emergency at any given time, even when that emergency changes and evolves through various stages. The instructions provided via the protocols 120 and received by the responders/recipients 140 via, for example, desktop applications or mobile devices, may be provided in a variety of forms, such as in written instructions, drawings, or animated instructions such as cartoons or photographs. Accordingly, the instructions may be in audio form, where the responder/recipient 140 can hear instructions on how to deal with the current emergency. Alternatively, the instructions may be in the form of a video, where the responder/recipient 140 can watch an instructional video on how to respond to the emergency.

According to various aspects of the present invention, the transmission between the dispatch center 110 and the responders/recipients 140 can be performed via a network 150 such as, for example, the Internet, or a local area network, or via transmission lines such as, for example, wired connections, wireless connections, or fiber-optic connections. Accordingly, through a single web-based user interface 110, a manager may be able to manage various emergency response protocol contents for any client emergency responders/recipients 140 in any geographical area of the country or of the world. Thus, if a single jurisdiction, geographical area, client or other user of the system requires an update with respect to a particular emergency, that jurisdiction, geographical area, client or other user can be updated in real time, or in a very short amount of time, directly from the emergency response protocol dispatch center 110. Also, according to various aspects of the present invention, as the user base grows, the dispatch center 110 may provide each client, geographical area, jurisdiction or other user of the system with regular and timely updates in response to specific emergencies that have happened or that are likely to happen in the future in those localized jurisdictions or geographical areas.

According to various aspects of the present invention, in order to transmit updated protocols in a timely manner to a broad range of clients or emergency responders, various platforms may be used to leverage common content managed at the dispatch center 110. As discussed above, a web-based application, according to various aspects of the present invention, allows for the use of a network, such as the Internet or a local area network, to provide client responders with updated protocols. For example, aspects of the present invention provide browser-based access via Internet Explorer, Firefox or Safari systems, and can be used on Windows, MacOS and Linux systems. According to various aspects of the present invention, a mobile version may also be provided to allow users of mobile devices to access the information provided at the dispatch center 110, the mobile devices being accessed wirelessly, with or without the use of a web-based platform.

It is to be understood that the above-described aspects are merely illustrative of numerous and varied aspects that may constitute applications of the principles of the present invention. Such other aspects include but are not limited to: a) emergency room protocols and procedures for hospitals; b) emergency/first aid protocols and procedures for schools; c) terrorist attack protocols and procedures for schools; d) emergency/first aid protocols and procedures for office workplace; e) terrorist attack protocols and procedures for office workplace; f) emergency/first aid protocols and procedures for malls; g) terrorist attack protocols and procedures for malls; h) emergency/first aid protocols and procedures for place of worship; i) terrorist attack protocols and procedures for place of worship; j) emergency/first aid protocols and procedures for airports, train stations, bus terminals; k) terrorist attack protocols and procedures for airports, train stations, bus terminals; l) audit, review, tax preparation protocols, checklists and procedures for certified public accountants; m) litigation, contract preparation, will preparation protocols, checklists and procedures for lawyers; n) state and federal court protocols and procedures for judges, lawyers; o) jury pool selection questionnaires in state and federal court systems; p) chemical spills, public service emergencies, bomb threats or dismantling, and nuclear evacuations procedures; q) emergency/first aid protocols and procedures for general public, and lifesaving CPR and Choking instructions; and r) Crime scene protocols and procedures for law enforcement officers and DNA collection protocols and procedures, among other aspects.

Other aspects of the present invention include providing recipients/responders 140 with information with respect to a wide variety of non-emergency applications. For example, manuals for the use of a computer, car repair manuals, instructions on how to set up drills for a sports team, and the like, can be transmitted to recipients/clients 140 via the dispatch center 110. These manuals, instructions or protocols 120 can also be updated at the dispatch center 110 and provided to various recipients/clients 140. Accordingly, aspects of the current invention may be utilized in non-emergency situations by exploiting the real time update of instructions based on access to a source database over a network.

Furthermore, aspects of the present invention may also be implemented and/or accessed via any of the following: a) any protocol, procedure and/or process (including professional and internal/private protocols); b) the invention can be accessed via any of computer, phone, or any mobile devices that is capable of outputting information either by displayed graphic text, pictures, or audible instructions; c) the specific instructions can be accessed for emergencies and/or non-emergency events; d) touch-screen, voice recognition, bio-security/user authorization and vision, among other means.

Figure 2:
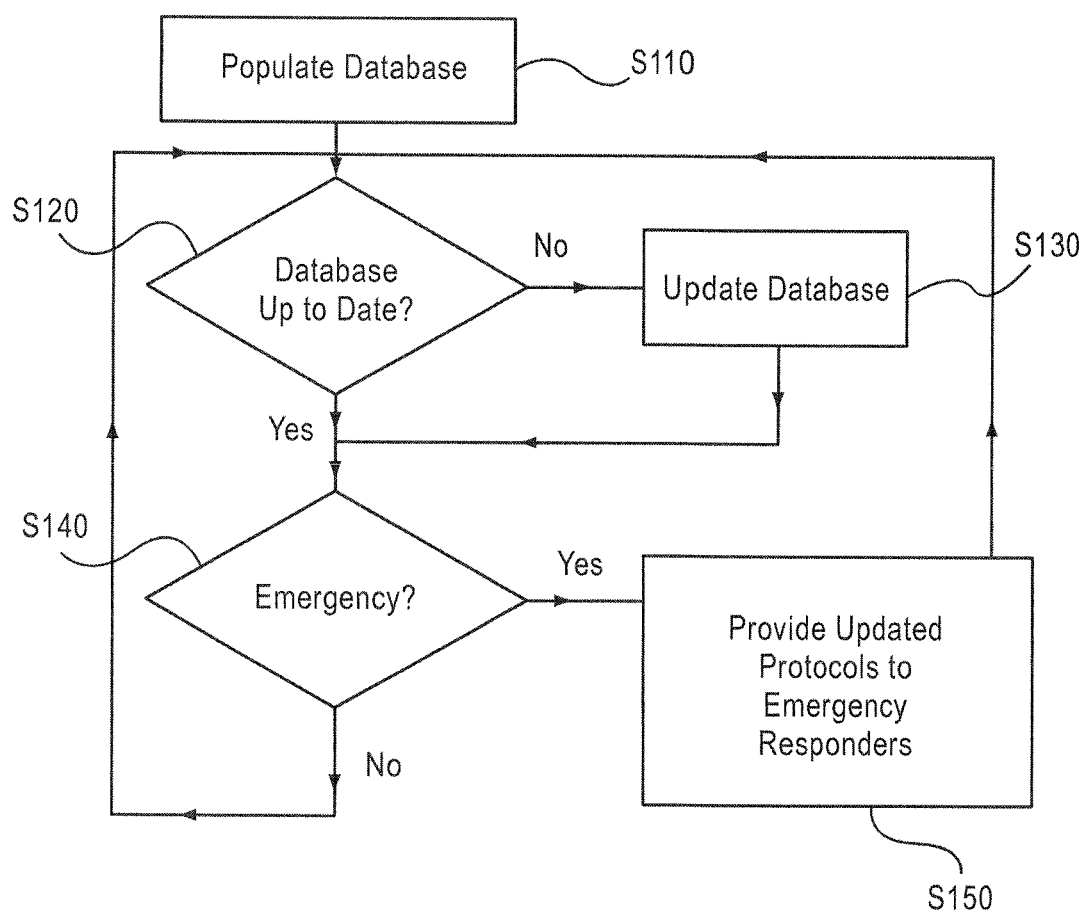
FIG. 2 is a flowchart illustrating an exemplary method for providing incident response in accordance with various exemplary aspects of the present invention.

FIG. 2 is a flowchart illustrating an exemplary method for providing incident response, in accordance with various exemplary aspects of the present invention. The method starts in S110, where a stat repository, such as a database, is populated. According to various aspects of the current invention, the database is populated with Emergency Medical Dispatch Protocol Reference Systems (EMDPRS) which provide response protocols for various medical emergencies. The database may also be populated with a variety of other response protocols for other types of emergencies, or for various types of needs that may not be emergencies. Next, the method continues to S120, where the database is checked to determine whether the contents of the database, i.e., the stored response protocols, are up to date, and whether the response protocols stored in the database correspond to the current scientific or otherwise accepted knowledge on how to respond to the various situations and emergencies to which the stored response protocols correspond. According to various aspects of the current invention, the database may be checked in S120 at regular intervals, or whenever new advances in response protocols, such as emergency response protocols, take place necessitating the update of the response protocols stored in the database.

If one or more of the response protocols stored in the database are determined to not be up to date, then the method continues to S130, where the response protocols stored in the database are updated to correspond to the latest scientific or otherwise accepted knowledge. For example, the response protocols may be updated timely and consistently with the requirements of the NHTSA, or with the latest developments in emergency response to the various stages of a pandemic influenza. Because updating a database can be accomplished in a minimal amount of time, even when the database is remotely located, updating the database in S130 can be accomplished almost instantaneously, so that the response protocols may be updated as soon as any development occurs that enhances a response protocol in response to an emergency. Accordingly, any emergency that is responded to via the response protocols stored in the database will be responded to pursuant to the latest knowledge on how to respond to that emergency.

According to various aspects of the current invention, the method in S140 determines whether there is an emergency. If there is an emergency, such as, for example, a pandemic influenza, a person choking, or a hurricane, the method continues to S150, where one or more of the updated response protocols that correspond to that emergency are provided to the emergency responders. Providing the protocols to the emergency responders may be accomplished via, for example, various devices such as desktop computers, portable computers, cell phones, personal digital assistants, mobile devices, other web-based systems, and the like, or any other data receiving device. According to various aspects of the present invention, providing the response protocols may also be performed in the form of written instructions, audio instructions, animated instructions such as a video, or animated drawings. Whether an emergency has occurred or not, the database is regularly checked to determine whether the response protocols stored in the database are up to date and correspond to the latest scientific and otherwise accepted knowledge.

According to various aspects of the current invention, during step S150, when one or more updated protocols are provided to an emergency responder such as an emergency medical dispatcher, the protocols may include a set of instructions to be followed by the responder. According to other aspects of the current invention, the emergency response protocol may include one or more questions provided to the responder in order to assess the proper response to the current emergency. According to various aspects, the instructions provided to the responder are based on the responses given by the responder. In other words, the choice of an emergency response protocol, or set of instructions to be followed by the responder to respond to the emergency, may depend on the responses given by the responder to the questions. As a result, the emergency response instructions provided to the responder correspond closely to the current emergency and provide the best possible response to the current emergency.

Alternatively, the responder may input information about the emergency without being prompted. Accordingly, the emergency response protocol provided to the responder, or set of response instructions, are provided on the basis of the information inputted by the responder. As a result, the emergency response protocol, or set of instructions to be followed by the responder to respond to the emergency, correspond closely to the current emergency and provide the best possible response to the current emergency.

Figure 3:
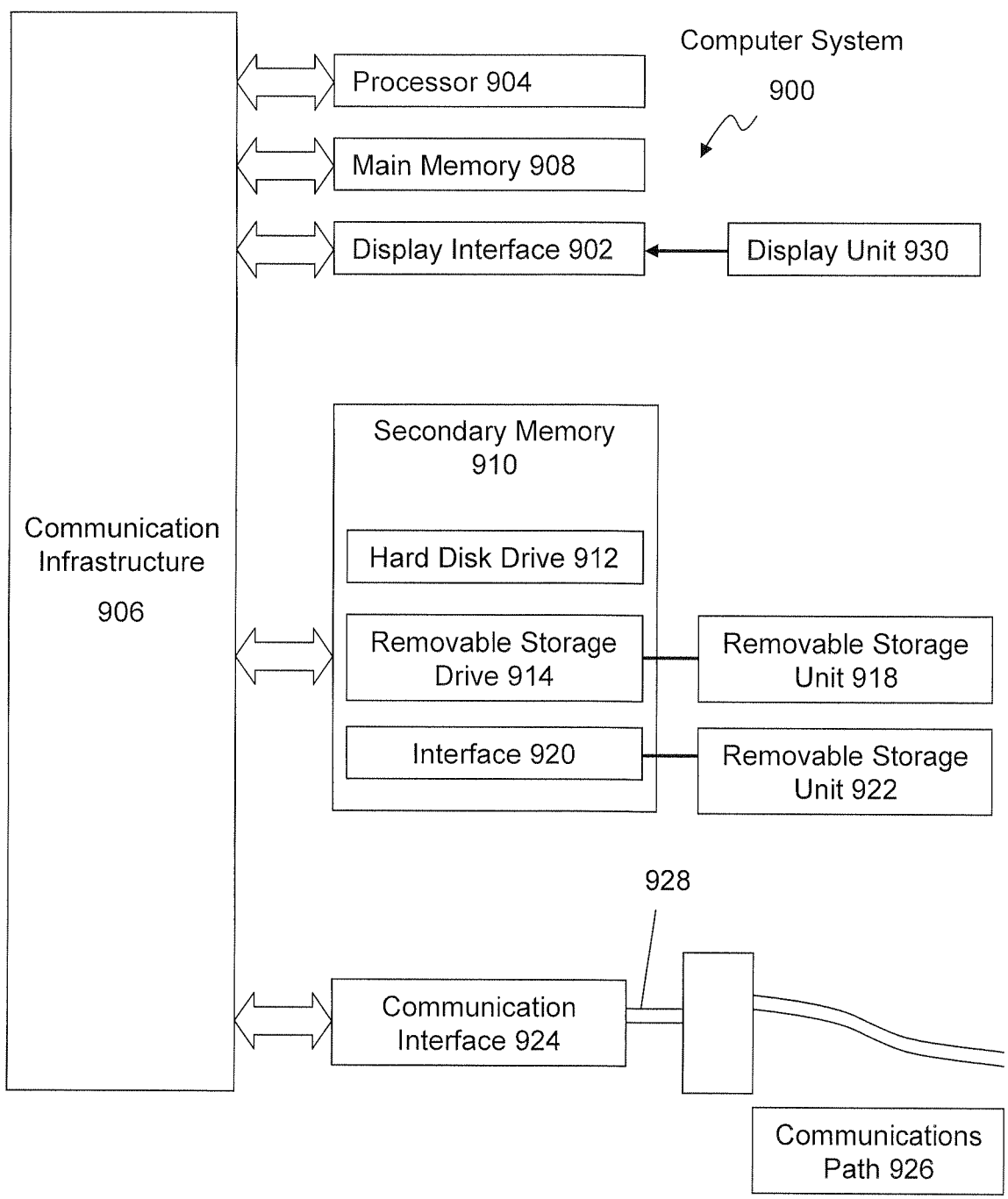
FIG. 3 presents an exemplary system diagram of various hardware components and other features, for use in accordance with various exemplary aspects of the present invention.

The present invention may be implemented using hardware, software, or a combination thereof and may be implemented in one or more computer systems or other processing systems. In one aspect, the invention is directed toward one or more computer systems capable of carrying out the functionality described herein. An example of such a computer system 900 is shown in FIG. 3.

Computer system 900 includes one or more processors, such as processor 904. The processor 904 is connected to a communication infrastructure 906 (e.g., a communications bus, cross-over bar, or network). Various software aspects are described in terms of this exemplary computer system. After reading this description, it will become apparent to a person skilled in the relevant art(s) how to implement the invention using other computer systems and/or architectures.

Computer system 900 can include a display interface 902 that forwards graphics, text, and other data from the communication infrastructure 906 (or from a frame buffer not shown) for display on a display unit 930. Computer system 900 also includes a main memory 908, preferably random access memory (RAM), and may also include a secondary memory 910. The secondary memory 910 may include, for example, a hard disk drive 912 and/or a removable storage drive 914, representing a floppy disk drive, a magnetic tape drive, an optical disk drive, etc. The removable storage drive 914 reads from and/or writes to a removable storage unit 918 in a well-known manner. Removable storage unit 918, represents a floppy disk, magnetic tape, optical disk, etc., which is read by and written to removable storage drive 914. As will be appreciated, the removable storage unit 918 includes a computer usable storage medium having stored therein computer software and/or data.

In alternative aspects, secondary memory 910 may include other similar devices for allowing computer programs or other instructions to be loaded into computer system 900. Such devices may include, for example, a removable storage unit 922 and an interface 920. Examples of such may include a program cartridge and cartridge interface (such as that found in video game devices), a removable memory chip (such as an erasable programmable read only memory (EPROM), or programmable read only memory (PROM)) and associated socket, and other removable storage units 922 and interfaces 920, which allow software and data to be transferred from the removable storage unit 922 to computer system 900.

Computer system 900 may also include a communications interface 924. Communications interface 924 allows software and data to be transferred between computer system 900 and external devices. Examples of communications interface 924 may include a modem, a network interface (such as an Ethernet card), a communications port, a Personal Computer Memory Card International Association (PCMCIA) slot and card, etc. Software and data transferred via communications interface 924 are in the form of signals 928, which may be electronic, electromagnetic, optical or other signals capable of being received by communications interface 924. These signals 928 are provided to communications interface 924 via a communications path (e.g., channel) 926. This path 926 carries signals 928 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 980, a hard disk installed in hard disk drive 970, and signals 928. These computer program products provide software to the computer system 900. The invention is directed to such computer program products.

Computer programs (also referred to as computer control logic) are stored in main memory 908 and/or secondary memory 910. Computer programs may also be received via communications interface 924. Such computer programs, when executed, enable the computer system 900 to perform the features of the present invention, as discussed herein. In particular, the computer programs, when executed, enable the processor 910 to perform the features of the present invention. Accordingly, such computer programs represent controllers of the computer system 900.

In an aspect where the invention is implemented using software, the software may be stored in a computer program product and loaded into computer system 900 using removable storage drive 914, hard drive 912, or communications interface 920. The control logic (software), when executed by the processor 904, causes the processor 904 to perform the functions of the invention as described herein. In another aspect, the invention is implemented primarily in hardware using, for example, hardware components, such as application specific integrated circuits (ASICs). Implementation of the hardware state machine so as to perform the functions described herein will be apparent to persons skilled in the relevant art(s).

In yet another aspect, the invention is implemented using a combination of both hardware and software.

Figure 4:
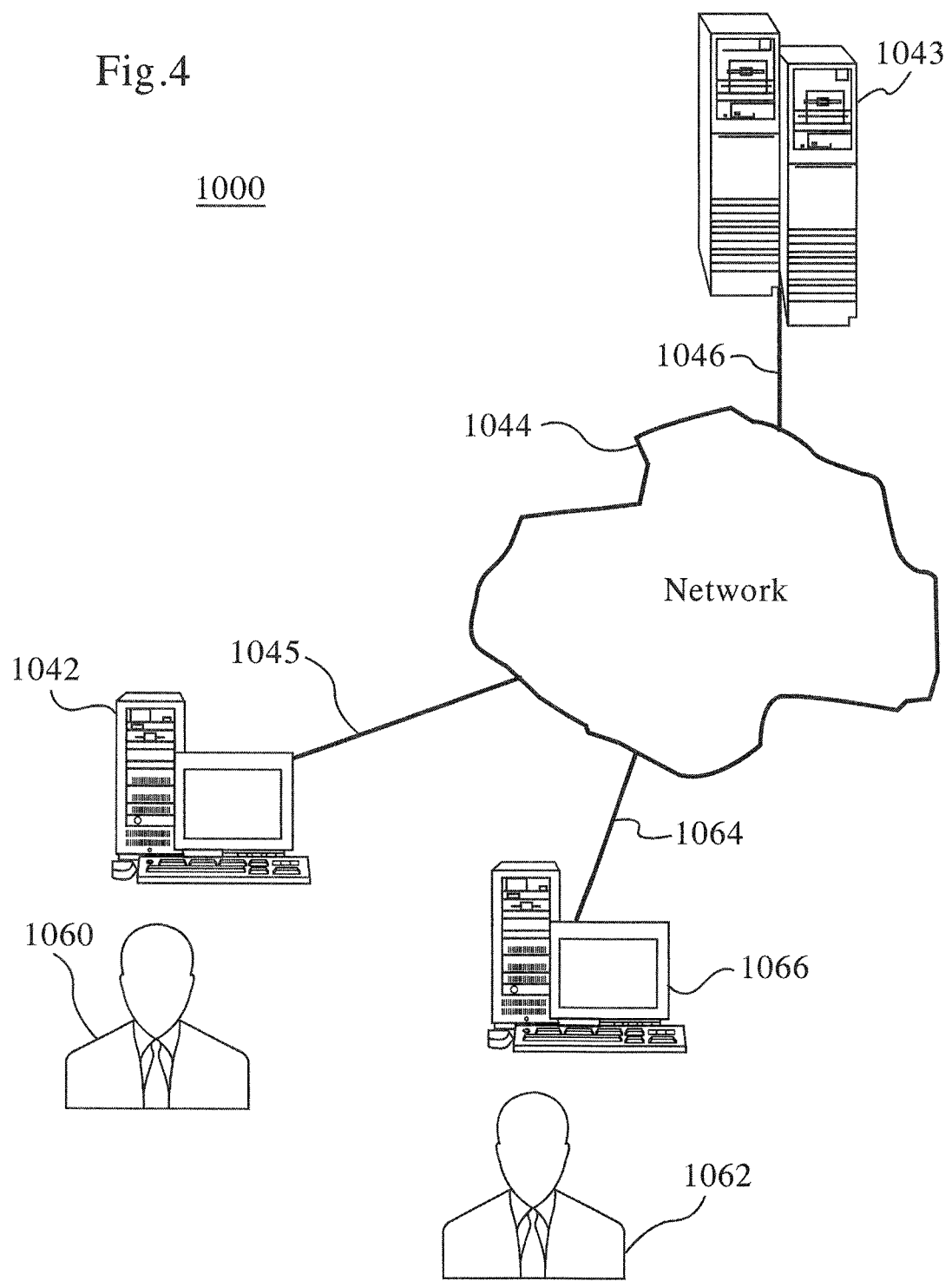
FIG. 4 is a block diagram of various exemplary system components, in accordance with an aspect of the present invention.

FIG. 4 shows a communication system 1000 usable in accordance with the present invention. The communication system 1000 includes one or more accessors 1060, 1062 (also referred to interchangeably herein as one or more "users") and one or more terminals 1042, 1066. In one aspect, data for use in accordance with the present invention is, for example, input and/or accessed by accessors 1060, 1064 via terminals 1042, 1066, such as personal computers (PCs), minicomputers, mainframe computers, microcomputers, telephonic devices, or wireless devices, such as personal digital assistants ("PDAs") or a hand-held wireless devices coupled to a server 1043, such as a PC, minicomputer, mainframe computer, microcomputer, or other device having a processor and a repository for data and/or connection to a repository for data, via, for example, a network 1044, such as the Internet or an intranet, and couplings 1045, 1046, 1064. The couplings 1045, 1046, 1064 include, for example, wired, wireless, or fiberoptic links. In another aspect, the method and system of the present invention operate in a stand-alone environment, such as on a single terminal.

Figure 5:
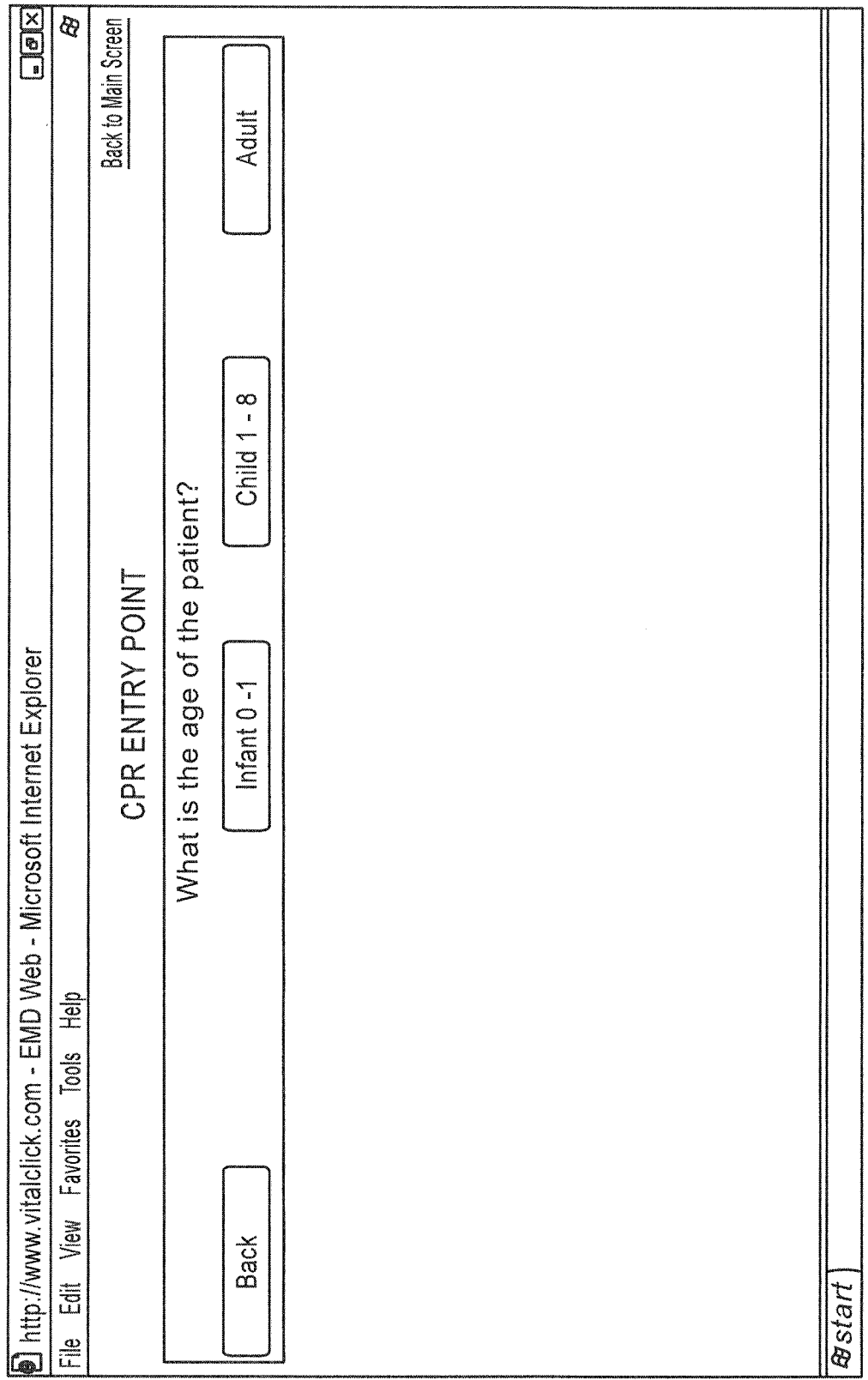
FIG. 5 is an illustration of an exemplary screen of a graphical user interface, according to various aspects of the present invention.

FIG. 5 is an illustration of an exemplary screen of a graphical user interface, according to various aspects of the present invention. In FIG. 5, the interface allows the emergency responder to select, for example, the age of the individual that is subject to the need or emergency. Once the age of the individual is selected, then the emergency responder may access other instruction screens targeted to responding to the need or emergency for the selected age bracket of the individual.

FIGS. 6A-6B are illustrations of exemplary screens of graphical user interfaces, in the English language and in the Spanish language, according to various aspects of the present invention. FIGS. 6A-6B provide a range of possible emergencies that may occur, and illustrate an example of an emergency responder interface that may be provided to an emergency responder early on in the emergency response process. These interfaces may be provided to the emergency responder in order for the responder to select the appropriate emergency to which the responder is confronted, and follow the instructions provided once the appropriate emergency has been selected. It should be noted that although FIGS. 6A and 6B show screens of graphical user interfaces in English and Spanish, screens of graphical user interfaces, according to various aspects of this invention, may be provided in any language. Also, instructions provided to an emergency responder may be provided in any language, including but not limited to English and Spanish.

FIG. 7 is an exemplary screen of a graphical user interface for emergency response instructions, according to various aspects of the present invention. In FIG. 7, the emergency responder is provided with a number of questions designed to elicit the best response possible to the emergency. According to various aspects of the present invention, later questions that are asked of the emergency responder depend on the responses provided by the responder to earlier questions. For example, if the responder answers "yes" to the first question "Is patient alert"?, the additional questions asked of the responder in order to most efficiently respond to the emergency may likely be different from the case when the responder had answered "no" to the same question.

Furthermore, while the present invention has been described in conjunction with the various aspects outlined above, various alternatives, modifications, variations, improvements, and/or substantial equivalents, whether known or that are or may be presently unforeseen, may become apparent to those having at least ordinary skill in the art. Accordingly, the exemplary aspects of the invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents.

What is claimed is:

1. A computer-implemented method for providing one or more response protocols from a protocol establishing entity to at least one recipient computer over a network, the recipient computer comprising a processor, the method comprising:
    determining the occurrence of an emergency via the at least one recipient;
    accessing, via a web-based application on the recipient computer over the network, at least one response protocol corresponding to the emergency from a database at the protocol establishing entity, wherein the at least one response protocol corresponds to a contemporaneous version of the response protocol stored in the database at the protocol establishing entity;
    providing, via the processor, the contemporaneous version of the response protocol over the network to the at least one recipient, wherein the contemporaneous version of the response protocol includes a set of instructions for the at least one recipient to follow when responding to the emergency;
    checking, at regular intervals, whether the contemporaneous version of the response protocol is up to date, and whether the contemporaneous version of the response protocol stored in the database corresponds to current scientific or otherwise accepted knowledge on how to respond to a situation or emergency to which the stored contemporaneous version of the response protocol corresponds;
    updating, via the network, the contemporaneous version of the response protocol stored in the database in near real time in response to determining that the contemporaneous version of the response protocol is not up to date based on information received regarding the emergency such that the database stores at least one updated response protocol; and
    providing, via the network, the at least one updated response protocol from the database to at least one other recipient via a web-based application on a second computer, the at least one updated response protocol including an updated set of instructions including an instructional video on how to respond to the emergency.

2. The method of claim 1, wherein the at least one recipient comprises at least one of an emergency operator and an individual experiencing the emergency.

3. The method of claim 1, wherein providing the contemporaneous version of the response protocol takes place via a mobile device accessible to the recipient.

4. The method of claim 1, wherein the recipient computer is one of a desktop computer, a portable computer, a cellular phone or a personal digital assistant.

5. The method of claim 1, wherein the at least one response protocol further comprises at least one of written instructions, animated images, still images, or audio instructions.

6. The method of claim 1, wherein providing the contemporaneous version of the response protocol over the network comprises providing the contemporaneous version of the response protocol over at least one of a web-based network, an Internet network, a local area network, or a wireless network.

7. The method of claim 1, wherein the contemporaneous version of the response protocol is provided to the at least one recipient on the basis of emergency information provided by the at least one recipient.

8. The method of claim 7, wherein the emergency information provided by the at least one recipient comprises one or more responses to one or more questions provided to the at least one recipient.

9. The method of claim 8, wherein the one or more questions are included in the at least one response protocol.

10. The method of claim 1, wherein:
    the at least one recipient provides information to an emergency responder; and
    the at least one response protocol is modified based on the information provided by the at least one recipient.

11. The method of claim 1, wherein the least one response protocol is accessed in one or more of a plurality of languages.

12. The method of claim 1, wherein the at least one recipient comprises an emergency medical dispatcher.

13. The method of claim 1, wherein the information received from the at least one recipient includes responses to questions regarding the emergency.

14. A system for providing one or more response protocols from a protocol establishing entity to at least one recipient computer over a network, the system comprising:
- means for determining the occurrence of an emergency via the at least one recipient;
- means for accessing, via a web-based application on the recipient computer over the network, at least one response protocol corresponding to the emergency from a database at the protocol establishing entity, wherein the at least one response protocol corresponds to a contemporaneous version of the response protocol stored in the database at the protocol establishing entity;
- means for providing the contemporaneous version of the response protocol over the network to the at least one recipient, wherein the contemporaneous version of the response protocol includes a set of instructions for the at least one recipient to follow when responding to the emergency;
- means for checking, at regular intervals, whether the contemporaneous version of the response protocol is up to date, and whether the contemporaneous version of the response protocol stored in the database corresponds to current scientific or otherwise accepted knowledge on how to respond to a situation or emergency to which the stored contemporaneous version of the response protocol corresponds;
- means for updating the contemporaneous version of the response protocol stored in the database in near real time in response to determining that the contemporaneous version of the response protocol is not up to date based on information received regarding the emergency such that the database stores at least one updated response protocol; and
- means for providing, via the processor, the at least one updated response protocol from the database to at least one other recipient via a web-based application on a second computer, the at least one updated response protocol including an updated set of instructions including an instructional video on how to respond to the emergency.

15. The system of claim 14, wherein the contemporaneous version of the response protocol is provided via a mobile device accessible to the recipient.

16. The system of claim 14, wherein the recipient computer is one of at least a desktop computer, a portable computer, a cellular phone or a personal digital assistant.

17. The system of claim 14, wherein the contemporaneous version of the response protocol further comprises at least one of written instructions, animated images, still images, or audio instructions.

18. The system of claim 14, wherein the network comprises at least one of a web-based network, an Internet network, a local area network, or a wireless network.

19. The system of claim 14, wherein the contemporaneous version of the response protocol is provided to the at least one recipient on the basis of emergency information provided by the at least one recipient.

20. The system of claim 19, wherein the emergency information provided by the at least one recipient comprises one or more responses to one or more questions provided to the at least one recipient.

21. The system of claim 20, wherein the one or more questions are included in the at least one response protocol.

22. A system for providing one or more response protocols from a protocol establishing entity to at least one recipient computer over a network, the system comprising:
- a processor;
- a user interface functioning via the processor; and
- a repository accessible by the processor; wherein
  - the occurrence of an emergency is determined via the at least one recipient;
  - at least one response protocol corresponding to the emergency at the protocol establishing entity is accessed from a database via a web-based application on the recipient computer over the network, wherein the at least one response protocol corresponds to a contemporaneous version of the response protocol stored in the database at the protocol establishing entity;
  - the contemporaneous version of the response protocol is provided to the at least one recipient, wherein the contemporaneous version of the response protocol includes a set of instructions for the at least one recipient to follow when responding to the emergency;
  - the contemporaneous version of the response protocol is checked, at regular intervals, to determine whether the contemporaneous version of the response protocol is up to date, and whether the contemporaneous version of the response protocol stored in the database corresponds to current scientific or otherwise accepted knowledge on how to respond to a situation or emergency to which the stored contemporaneous version of the response protocol corresponds;
  - the contemporaneous version of the response protocol is updated in the database in near real time in response to determining that the contemporaneous version of the response protocol is not up to date based on information received regarding the emergency such that the database stores at least one updated response protocol; and
  - the at least one updated response protocol is provided, from the database, to at least one other recipient via a web-based application on a second computer, the at least one updated response protocol including an updated set of instructions including an instructional video on how to respond to the emergency.

23. The system of claim 22, wherein the processor is housed on a terminal.

24. The system of claim 23, wherein the terminal is selected from a group consisting of a personal computer, a minicomputer, a main frame computer, a microcomputer, a hand held device, and a telephonic device.

25. The system of claim 22, wherein the processor is housed on a server.

26. A computer program product comprising a non-transitory computer usable medium having control logic stored therein for causing a computer to provide one or more response protocols from a protocol establishing entity to at least one recipient over a network, the control logic comprising:
- first computer readable program code means for determining the occurrence of an emergency via the at least one recipient;
- second computer readable means for accessing, via a web-based application on the recipient computer over the network, at least one response protocol corresponding to the emergency from a database at the protocol establishing entity, wherein the at least one response protocol corresponds to a contemporaneous version of the response protocol stored in the database at the protocol establishing entity;

third computer readable means for providing the contemporaneous version of the response protocol over the network to the at least one recipient, wherein the contemporaneous version of the response protocol includes a set of instructions for the at least one recipient to follow when responding to the emergency;

fourth computer readable means for checking, at regular intervals, whether the contemporaneous version of the response protocol is up to date, and whether the contemporaneous version of the response protocol stored in the database corresponds to current scientific or otherwise accepted knowledge on how to respond to a situation or emergency to which the stored contemporaneous version of the response protocol corresponds;

fifth computer readable means for updating the contemporaneous version of the response protocol stored in the database in near real time in response to determining that the contemporaneous version of the response protocol is not up to date based on information received regarding the emergency such that the database stores at least one updated response protocol; and sixth computer readable means for providing, via the processor, the at least one updated response protocol from the database to at least one other recipient via a web-based application on a second computer, the at least one updated response protocol including an updated set of instructions including an instructional video on how to respond to the emergency.

* * * * *